Figure 1:
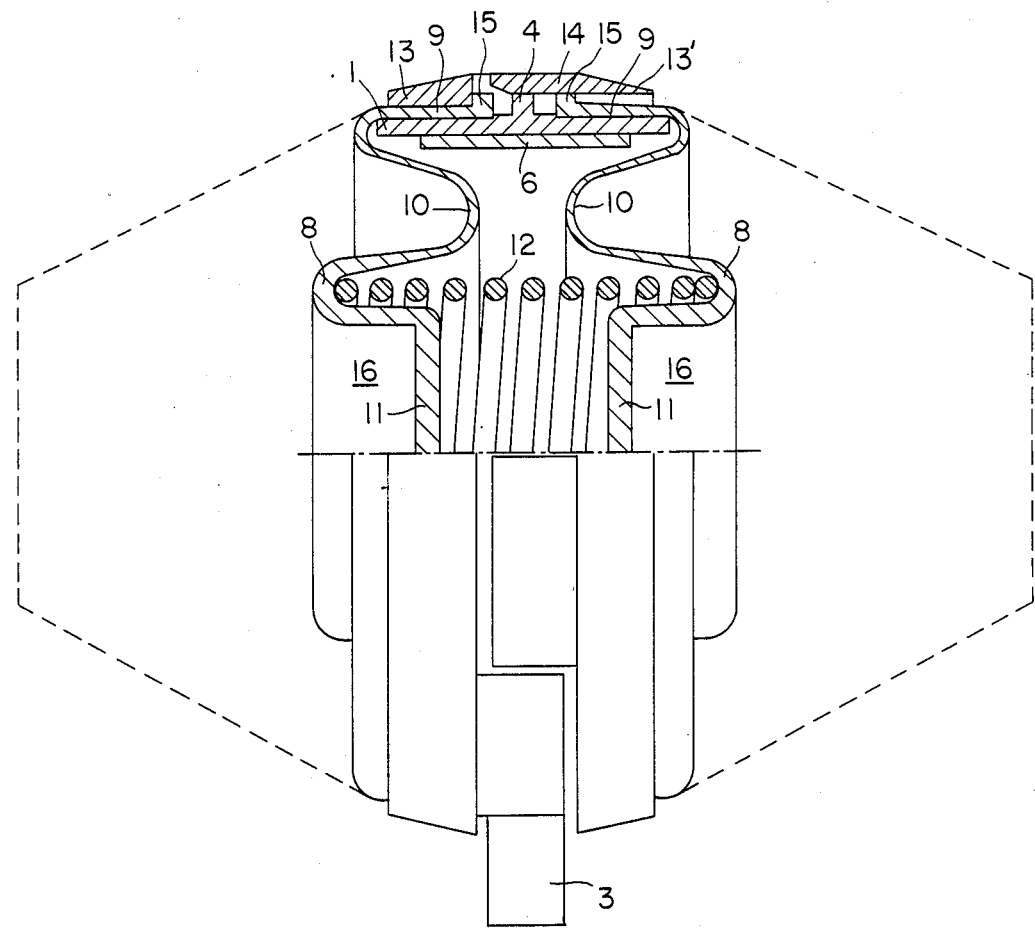

United States Patent [19]

Ekbladh et al.

[11] Patent Number: 4,671,791
[45] Date of Patent: Jun. 9, 1987

[54] SUCTION PUMP

[76] Inventors: Fred Vage G. Ekbladh, Rosengatan 9, S-434 00 Kungsbacka; Håns Tillander, Humlegårdsgatan 3, S-412 74 Göteborg, both of Sweden

[21] Appl. No.: 675,535

[22] Filed: Nov. 28, 1984

[30] Foreign Application Priority Data

Nov. 29, 1983 [SE] Sweden ............................ 8306577

[51] Int. Cl.⁴ .................................................. A61M 37/00
[52] U.S. Cl. ...................................... 604/133; 604/73; 417/472
[58] Field of Search .................... 604/131, 133, 73, 74, 604/93, 891, 141, 151, 153, 134, 317, 319, 247, 142, 146; 417/472, 473, 474

[56] References Cited

U.S. PATENT DOCUMENTS

| | | | |
|---|---|---|---|
| 603,564 | 5/1898 | Hoover | 604/135 |
| 1,029,496 | 6/1912 | Garlock | 417/472 |
| 3,376,868 | 4/1968 | Mondiadis | 604/133 |
| 3,542,026 | 11/1970 | Bledsoe | 604/247 |
| 3,774,611 | 11/1973 | Tussey et al. | 604/133 |
| 3,779,243 | 12/1973 | Tussey et al. | 604/133 |
| 4,058,173 | 11/1977 | May | 604/133 |
| 4,429,693 | 2/1984 | Blake et al. | 604/133 |

Primary Examiner—John D. Yasko
Attorney, Agent, or Firm—Brumbaugh, Graves, Donohue & Raymond

[57] ABSTRACT

The present invention relates to a suction pump, preferably for suction drainage or body cavities with regard to accumulated liquid after a surgical incision made, and comprising an expandable, flexible container, whereby two substantially symmetric lid parts are attached to each other, comprising at least one rigid ring (1,13) and a flexible casing (8), an expandable spring (12) arranged between said casings (8) of the lid parts, an inlet opening (2,6) provided with a membrane valve (7) and an outlet opening (3) to which an one-way valve is arranged to be connected to provide for an one-way current out off the pump of air and/or liquid.

2 Claims, 2 Drawing Figures

SUCTION PUMP

TECHNICAL FIELD

The present invention relates to a suction pump, preferably to be used in suction drainage of body cavities with regard to accumulated liquid after a surgical incision has been made.

The object of the present invention is to obtain a possibility to apply a suction having a constant vacuum to a drainage tube for the suction of liquid by means of an intermittently acting suction device.

BACKGROUND OF THE INVENTION

It is previously known to use different types of suction pumps at the suction drainage of body cavities with regard to body liquid accumulated therein after a surgical incision. One such known pump is a bellows pump made of a polymeric material, which pump after having been compressed endeavors to stretch out again, to expand, whereby a vacuum is created in a drainage tube connected to the bellows pump. When the pump has reassumed its original shape and contains drained liquid it can be recompressed, whereby liquid drained is pressed out through a further tube connected to the pump. It has turned out that the bellows pump thus known in the art provides a decreasing vacuum in the drainage tube, which in turn leads to an unacceptable reduced transport of accumulated liquid.

One has thus requested a suction pump which provides a more constant vacuum during its whole period of action. One has also wished to have a suction pump which is smaller and easier to handle than that known one, as it has turned out that this is difficult to hide in the clothes, and, further demands a careful instruction in order to be handled. Correctly handled the known device is per se simple to handle.

DISCLOSURE OF THE PRESENT INVENTION

It has now been found possible to solve this problem by the present invention, which is characterized by two substantially symmetric casings fixed to each other, comprising at least one rigid ring and a flexible covering part, an expanding spring arranged between the covering parts of the casings one inlet opening provided with a membrane valve, and an outlet opening provided with an one-way valve to give a one-way current out of the pump of air and/or liquid.

Further characteristics are evident from the accompanying claims.

The present invention will be described in more detail in the following with reference to the accompanying drawings, wherein FIG. 1 shows a preferred embodiment of the invention seen from the side, whereby a part thereof is shown in cross-section.

Figure 2:
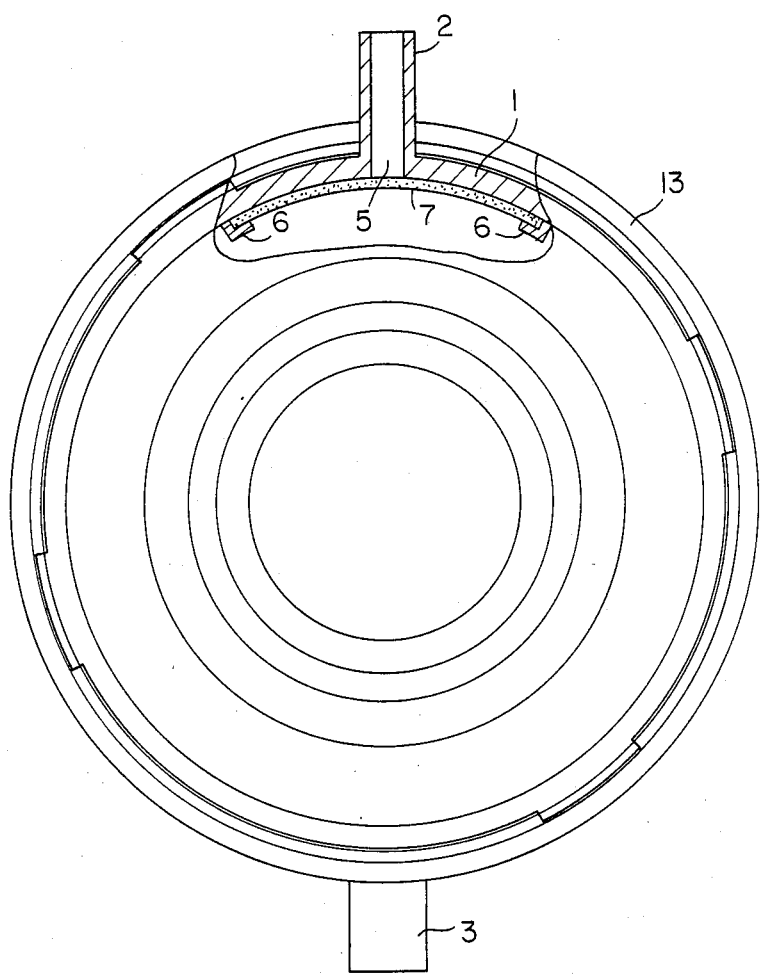

FIG. 2 shows the embodiment of FIG. 1 seen from one of its short sides.

1 denotes a cylindrical ring provided with an inlet connector 2 and an outlet connector 3. The ring 1 is on its outside provided with a radially directed flange 4. On each side of the inlet opening 5 of the inlet connector 2 two holders 6 are arranged. The holders 6 are arranged to receive a prestrained membrane 7 between them, which membrane 7 consists of a disc made of rubber or a thermoplastic material. Two symmetrical casings 8 are passed over the ring 1, which casings 8 comprise an outer circular part 9, an intermediate expansion part 10, and a hub part 11. The hub part 11 has a depression 16 being concentric with the circular outer part 9, which depression is arranged to control a spring 12 arranged between said casings 8. The casings 8 are kept in place by means of two outer, preferably symmetric, rings 13 and 13' slipped over them, which rings are provided with resilient tongues 14 provided with protrusions arranged to catch the flange 4 of the ring 1. In order to fix the casings 8 by means of the outer rings 13 and 13' the outer parts 9 of the casings 8 are provided with an outwardly directed flange or ring-shaped protrusion 15. The fit between the ring 1, the casings 8, and the outer rings 13 and 13' is such that it is airtight. The casings 8 are made of a flexible thermoplastic material. The depression 16 of the hub part 11 can receive aiding means (not shown) for compression and/or assemblying the two casings 8 to a position as shown with a full drawn line in FIG. 1. A dotted line shows the position of the casings 8 when they have been pressed out, aside, by the spring 12. The outlet connector 3 is provided with an one-way valve (not shown) which can be a lip-valve arranged in a deposit container (not shown) connected to the connector 3.

In usage the inlet connector 2 is connected to a drainage tube, the casings 8 are compressed together, whereby when these are left the membrane is bent somewhat inwardly and admits passage of drained liquid into the pump. When this has expanded to full volume it can be recompressed, whereby the membrane 7 closes the inlet opening 2 and drained liquid passes out through the outlet connector 3 and its one-way valve. The current of liquid is thus one-way.

It has turned out that the pump gives a substantial vacuum in the drainage tube during its whole expansion phase. This is particularly achieved by the bobbin-shaped construction of the spring 12, which construction gives an even springpower over its whole range of expansion.

At the production of the casings 8 the sprue can be placed centrally in the hub part 11. The sprue residue can thereby be left, and in one embodiment of the invention the hub part 11 is made so thin that it will function as a membrane having the sprue residue in the centre. When vacuum has been applied to the pump, i.e., after compression, this thinned hub part 11 is sucked into the pump. A signal disc can thereby be placed onto the sprue residue, whereby this disc, when the vacuum applied, is hidden in the depression of the hub part 11, and when vacuum no longer is at hand, the signal disc is shown above this depression.

We claim:

1. A suction pump adapted for drainage of accumulated fluid in a body cavity or surgical wound of a patient, comprising:
   (a) a pair of opposed casings of a generally circular shape around an axis of rotation, each of said casings having (i) a hub portion surrounding said axis and having an axially positioned depression therein, (ii) a flexible portion surrounding said hub portion, and (iii) a retaining ring portion surrounding said flexible portion at the outer periphery thereof;
   (b) first and second cylindrical rings having diameters corresponding generally to the outer periphery of said opposed casings, the retaining ring portions of said casings being interposed between said rings, and said rings being adapted to clamp said retaining ring portions in an air-tight seal and to form thereby an enclosed space between said casings, (c) spring means within the enclosed space adjacent to and surrounding said depression in the hub portion wherein said spring means resiliantly urges said casings away from each other, whereby, when said spring means is fully compressed, said casings, including said flexible portion, are in a first position of minimum enclosed volume, and, whereby when said spring means is fully expanded, said casings, including said flexible portions, are in a second position of maximum enclosed volume, (d) an inlet passage through said first and second rings, for communication of fluid to be drained from said patient to said enclosed space, said inlet passage being provided with a valve means effective to allow passage of fluid from said patient to said enclosed space and to close against said fluid passage in the opposite direction, and (e) an outlet passage through said first and second rings for discharge of fluid contained in said enclosed space when said casings are compressed to said first position, said outlet passage being provided with a one-way valve adapted to open as said casings are compressed to said first position and to close while said spring means is expanding said casings to said second position.

2. A suction pump according to claim 1, further comprising a third ring positioned within the enclosed space, concentric with said first and second rings.

* * * * *